United States Patent
Fogel

[11] Patent Number: 6,117,877
[45] Date of Patent: Sep. 12, 2000

[54] METHOD FOR TREATING PAINFUL CONDITIONS OF THE ANAL REGION AND COMPOSITIONS THEREFOR

[75] Inventor: Barry S. Fogel, Waban, Mass.

[73] Assignee: Synchroneuron, LLC, Waban, Mass.

[21] Appl. No.: 09/258,828

[22] Filed: Feb. 25, 1999

Related U.S. Application Data

[63] Continuation of application No. 09/031,858, Feb. 27, 1998.

[51] Int. Cl.$^7$ .................................................. A61K 31/505
[52] U.S. Cl. .......................... 514/260; 514/23; 514/331; 514/400; 514/537; 514/626; 514/627; 514/651
[58] Field of Search .............................. 514/627, 23, 626, 514/537, 331, 400, 651, 260

[56] References Cited

U.S. PATENT DOCUMENTS 4,945,084  7/1990  Packman .
5,447,947  9/1995  Campbell .
5,854,291  12/1998  Laughlin et al. .

OTHER PUBLICATIONS

CA 128: 119698, Samejima et al., JP 10001331 A2, Abstract, Jan. 6, 1998.

*Primary Examiner*—Rebecca Cook
*Attorney, Agent, or Firm*—Choate, Hall & Stewart

[57] ABSTRACT

Method and composition for treating painful conditions of the anorectal region. The compositions include a combination of an α-adrenergic blocker and sucralfate, a combination of α-adrenergic blocker and lidocaine, and a combination of an α-adrenergic blocker, lidocaine, and sucralfate. Alternatively, the composition may contain only an α-adrenergic blocker. Additional active ingredients for reduction of anal pain may be added to the composition, particularly capsaicin. The compositions may be included in a petrolatum base along with a water soluble lubricant. These compositions have been found effective in treating painful conditions in the anal region, such as anal fissures, inflamed or recently thrombosed hemorrhoids, and chronic anal pain.

22 Claims, No Drawings

METHOD FOR TREATING PAINFUL CONDITIONS OF THE ANAL REGION AND COMPOSITIONS THEREFOR

PRIORITY CLAIM

The present application is a continuation-in-part of co-pending application Ser. No. 09/031,858, filed Feb. 27, 1998, pending the entire contents of which are incorporated herein by reference.

BACKGROUND OF THE INVENTION

This invention relates to methods and compositions for treating painful conditions of the anal region and more particularly for treating anal fissures, thrombosed or inflamed hemorrhoids, pain associated with the after effects of anal surgery (such as rubber-band ligation of internal hemorrhoids) and chronic anal pain.

Pain in the anal region is often associated with spasm of the anal sphincter. Sphincters are circular groups of smooth muscle that control the orifices of hollow organs. Sphincters are present throughout the gastrointestinal (GI) tract and function to control the passage of materials through this system of the body. When constricted, the sphincters close orifices leading to the hollow organs, such as the stomach, intestine, anus, etc. In order for the sphincter to open, the muscles must relax.

The sphincter that closes the anus (sphincter ani) consists of two sphincter muscle groups. The external anal sphincter is a thin flat plane of striated muscle fibers adherent to the integument surrounding the margin of the anus. The internal anal sphincter (IAS) is a ring of smooth muscle that surrounds the lower extremity of the rectum. Local inflammation can cause sphincter spasm and consequent pain. Dilation of the veins in the anorectal area results in the condition known as hemorrhoids. Frequently, hemorrhoids are accompanied by bleeding, thrombosis, inflammation, and pain in the rectal area. The pain associated with hemorrhoids is due primarily to the combination of inflammation adjacent to the anal sphincters, and spasm of the internal anal sphincter.

Anal fissures are breaks in the integrity of the anal mucosa. Anal fissures can be an extremely painful condition. The primary reason for severe pain is spasm of the internal anal sphincter (IAS). This spasm causes ischemia, which both produces pain and interferes with healing (Sharp, *American Journal of Surgery,* 1996 171:512–515; Schouten et al., *Scandinavian Journal of Gastroenterology,* Supplement, 1993 31(218):78–81). Spasm of the anal sphincter, as noted above, also plays a role in the pain of inflammatory conditions of the anal region, such as inflamed or recently thrombosed hemorrhoids (Janicke & Pundt, *Emergency Medicine Clinics of North America,* 1996 14:757–788). (See also, Madoff, *New England Journal of Medicine,* January 22, 1998, 338,(40):217–220). Prolonged spasm of the IAS causes ischemia of the muscle, generating a chemical stimulus to nociceptive nerves in the anal region.

Effective treatments for anal fissures, whether medical or surgical, involve both relaxation of the spastic muscle and relieving pressure in the anal canal, which is largely determined by the intensity of the contraction of the IAS. These treatments include lateral sphincterotomy, injection of the sphincter with botulinum toxin (Maria et al., *Ann Surg,* 1998 November, 228(5):664–9), and application of nitroglycerin ointment (Manookian et al.; *Ann Surg* 1998 October, 64(10):962–4; Lund and Scholefield *Br J Surg* 1996 October, 83(10):1335–44; Schouten et al.; *Scand J Gastroenterol Suppl* 1996 218:78–81). A recent review by Sharp (Sharp, *Am J Surg* 1996 May,171(5):512–5) of treatment for chronic anal fissures recommends beginning with nitroglycerin ointment. If the fissure has not healed in six weeks, botulinum toxin injections are given. That review notes that "considerable educational effort is required to successfully adjust the dose" of nitroglycerin (Sharp, 1996, supra.). It states that nitroglycerin "will often eliminate the severe pain of fissure-in-ano in 1 day". Schouten et al. (1993, supra.) used topical isosorbide dinitrate to treat chronic anal fissures, attaining pain relief" within 10 days". Lund & Scholefield (*Lancet,* 1997 349:11–14) reported a randomized controlled trial of 0.2% nitroglycerin ointment for anal fissure. At 2 weeks, pain on defecation, as measured by a visual analogue scale (0=no pain, 100=worst pain ever), averaged 33.5 in the treated group, compared with 48.0 in a group treated with placebo, and 73.0 in the same patients at baseline.

Nitroglycerin has been reported to diminish the pain of thrombosed external hemorrhoids (Gorfine, *Dis Colon Rectum* 1995 May, 38(5):453–6). The final common pathway for the relaxation of the IAS in response to various stimuli is the release of nitric oxide. Nitric oxide is a known modulator of sphincter tone and acts as an antispasmodic by bringing about a concentration-dependent reduction in the resting tension of IAS. This was demonstrated in vitro by Rattan et al. (*Am. J. Physiol.,* 1992 262:G107–112) in a muscle strip preparation. It is thought that nitric oxide or nitric oxide-liked substances serve as important control mechanisms for the general phenomenon of gastrointestinal adaptive relaxation. In U.S. Pat. No. 5,504,117, Gorfine establishes the use of nitric oxide donors in general, alone or in combination with local anesthetics, for the treatment of anal fissures. Subsequently, in U.S. Pat. No. 5,693,676, Gorfine further establishes the use of nitric oxide donors for treatment of anal disorders.

Despite positive clinical trials, nitroglycerin has not been universally accepted as a treatment for anal fissure. According to an experienced rectal surgeon and a gastroenterologist with a special interest in the colon and rectum (Wrobleski, 1997, personal communication), many patients simply do not get adequate pain relief from nitroglycerin, even in concentrations as high as 0.5%. My experience with one patient was that nitroglycerin relieved the pain, but only at a concentration that caused a significant headache. Moreover, the patient's anal pain recurred within two hours. The reviews cited above point out additional problems, including the full day sometimes needed before pain is relieved, and compliance problems because of headaches and the need for frequent dosage adjustments (Sharp, 1996, supra.). The problems of inadequate relief, short duration of relief, and intolerance of the drug were also described in a recent prospective study of 19 outpatients with chronic anal fissure (Watson et al., *British Journal of Surgery,* 1996 83:771–775). In this study, of the 15 patients who used nitroglycerin for 6 weeks and returned for a second visit, only 6 were symptom-free.

Several additional approaches are known for relaxation of the IAS. In U.S. Pat. No. 5,595,753, Hechtman sets forth the use of L-arginine as an active ingredient in topical formulations and methods for treating hemorrhoidal pain and sphincter spasm in the gastrointestinal tract. L-arginine acts to increase nitric oxide production. Application of L-arginine in a topical carrier directly to the affected area relaxes sphincter tension and relieves hemorrhoidal pain in approximately 10 minutes. A separate approach, described by Parischa and Kallo in U.S. Pat. No. 5,437,291, makes use of direct injections of botulinum toxin into the affected area for treatment of gastrointestinal muscle disorders and other smooth muscle dysfunction. They report that the benefits of botulinum toxin injection appear to be sustained for several months.

A second source of pain in anal fissures and related conditions is inflammation and irritation of inflamed areas by the fecal stream. In U.S. Pat. No. 4,945084 and U.S. Pat. No. 5,478,814, both by Packman, the use of sucralfate and other related polysaccarides is taught for the treatment of anal conditions, where sucralfate forms an antiinflammatory, antibacterial, and protective coating of the skin lesion. Sucralfate is a polysaccharide originally marketed as a treatment for peptic ulcer disease. Sucralfate has since been used with success for a variety of ulcerative conditions of the skin and of mucosa, including skin ulcers and excoriations (Hayashi et al., *J Pediatr Surg,* 1991 November, 26(11): 1279–81), solitary rectal ulcers (Spiliadis et al., *Gastrointestinal Endoscopy,* 1989 35:131–132), and ulcerative colitis (Riley et al., *Scandinavian Journal of Gastroenterology,* 1989 24:1014–1018). Sucralfate, when applied to a damaged mucosa, forms an adherent film that protects the mucosa and promotes healing (Kochhar et al., *Diseases of the Colon and Rectum,* 1990 33:49–51). In addition, sucralfate lowers local levels of the inflammatory mediator $PGE_2$ (Zahavi et al., Diseases of Colon and Rectum, 1989 32:95–98).

Lidocaine, a topical anesthetic, has been used as a treatment for another painful rectal condition, ulcerative proctitis (Bjorck et al., *Scandinavian Journal of Gastroenterology,* 1989 24:1061–1072). It has also been recommended to relieve pain sufficiently to permit rectal examination of patients with fissures. However, it is not uncommon for pain relief to be insufficient, so that the physician must resort to anesthesia or intravenous sedation, or wait for improvement with conservative treatment (Janicke & Pundt, 1996, supra.)

Sucralfate, a polysaccharide originally marketed as a treatment for peptic ulcer disease, has since been used with success for a variety of ulcerative conditions of the skin and of mucosa, including pressure ulcers (bedsores), solitary rectal ulcers (Spiliadis et al., *Gastrointestinal Endoscopy,* 1989, 35:131–132), and ulcerative colitis (Riley et al., *Scandinavian Journal of Gastroenterology,* 1989, 24:1014–1018). It has not been reported as a treatment for anal fissures. Sucralfate, when applied to a damaged mucosa, forms an adherent film that protects the mucosa and promotes healing (Kochhar et al., *Diseases of the Colon and Rectum,* 1990 33: 49–51). In addition, sucralfate lowers local levels of the inflammatory mediator $PGE_2$ (Zahavi et al., *Diseases of Colon and Rectum,* 1989 32:95–98).

In co-pending, commonly-owned U.S. patent application Ser. No. 09/031,858, incorporated by reference herein, I show that sucralfate, together with nitroglycerin, lidocaine, or both, is efficacious for the treatment of anal fissures, and inferred its utility for other painful conditions of the anal region. I suggested that the three ingredients would show synergy in the treatment of these disorders, and presented several cases in which they were particularly effective in relieving pain and promoting healing. Experiments with patients with anal fissures further demonstrated that all three ingredients together produced a better analgesic effect than any two ingredients together. Topical nitroglycerin has become a standard treatment option for anal fissures by rectal surgeons. However, use of nitroglycerin is limited by the frequent occurrence of headache, which often requires discontinuation of the drug. Moreover, it is not always effective in relieving the pain of anal fissures.

A recent study demonstrates the limitations of nitroglycerin alone in the treatment of anal fissure. Nitroglycerin ointment, approximately 200 mg at a time, was applied topically in different concentrations to the anal margin in patients with chronic anal fissure, both observing fissure healing and monitoring the effect of nitroglycerin on the maximum resting pressure (P) of the internal anal sphincter. (Watson et al., *Br. J. Surg.* 83:771–5, June, 1996). Nineteen patients with chronic anal fissure were treated with ointment containing increasing concentrations of nitroglycerin (0.2–0.8%), until MRP was reduced by more than 25%. The investigators prescribed for each patient nitroglycerin ointment with the minimum concentration of nitroglycerin that reduced that patient's MRP by at least 25%. The patient applied the ointment to the anal area twice daily for 6 weeks. At 6 weeks, the fissures had healed in 9 patients. Six required sphincterotomy and four were lost to follow-up. Eight of the nine patients with healed fistula required a nitroglycerin concentration well above the minimum concentration of nitroglycerin capable of reducing the resting pressure (0.3% v. 0.2%). Sixteen patients were resistant to the usually effective dose of 0.2% nitroglycerin. Three patients experienced tachyphylaxis, and the duration of action of nitroglycerin was less than the 12 hours reported in control patients. Two patients did not complete the study because of headache.

There exists the need to find an ingredient not previously used the topical treatment of painful conditions of the anal region, that can reduce IAS pressure at non-toxic dosages. Such an ingredient could increase the efficacy of combination preparations for topical treatment of painful anal conditions. The present application describes new pharmaceutical compositions for the treatment of painful conditions of the anal region.

SUMMARY OF THE INVENTION

One aspect of the invention is a composition comprising an α-adrenergic blocker alone at an effective and tolerable dose. Another aspect of the present invention is a composition comprising the combination of an α-adrenergic blocker together with sucralfate. Yet another aspect is a composition comprising a combination of an α-adrenergic blocker together with a local anesthetic (preferably lidocaine). In addition, the inventive composition may combine α-adrenergic blocker, together with sucralfate and a local anesthetic to achieve a synergistic effect. These compositions have analgesic properties and are useful for treatment of anal fissures and other painful conditions of the anal region.

In other preferred embodiments, the compositions of the present invention are combined with one or more of a variety of other active agents for increased analgesic effect. One particularly preferred active ingredient is capsaicin. According to the present invention, capsaicin may be added to any composition for treatment of anal pain. Continued capsaicin treatment, may be effective in reducing some of the reflex contractions of the rectum that can create an uncomfortable sense of fecal urgency in an individual with a painful anal condition. Capsaicin can be co-administered with a local anesthetic agent to diminish the burning sensation that accompanies its initial application to skin or mucosa. In other preferred embodiments, any of a number of active ingredients that may have a variety of effects, both analgesic and non-analgesic, can be added to compositions of the present invention.

The combination of three or more active ingredients in a topical preparation will relieve pain and spasm in a synergistic manner, allowing lower concentrations of individual active ingredients, and diminishing toxicity. Specifically, the use of multiple ingredients reduces the necessary dose of the α-adrenergic agent, thereby minimizing the likelihood of hypotension or headache as a side effect.

Another aspect of the invention provides compositions wherein an α-adrenergic blocker (or capsaicin) is used to replace the active agent in various currently marketed over-the-counter compositions for treatment of anorectal conditions. For example, α-adrenergic blocker can be used to replace the active agents in known, over-the counter products including "Preparation H", "Anusol" and similar preparations. Alternatively an α-adrenergic blocker may be co-administered in conjunction with such preparations for improved treatment of anal pain.

The present compositions can be administered in any of a wide variety of forms. These compositions may be combined in a petrolatum base along with a water soluble lubricant such as K-Y™ Jelly. By way of further example, these compositions may be delivered in any form that may be applied topically to the anal region. Alternatively, the compositions of the present invention may be applied to any part of the body.

DEFINITIONS

"Effective": "Effective" as used herein in reference to dose refers to the administration of a specific amount of a pharmacologically active agent tailored to each individual patient manifesting symptoms of anorectal disease, sufficient to cause a reduction or improvement in any of the associated symptoms, with tolerable adverse effects. A person skilled in the art will recognize that the optimal dose of a pharmaceutical composition administered will vary from one individual to another. When considering a topical preparation for anorectal use, dosage in individual patients— regarding the concentration of the ingredients, the amount to be applied with each application, and the frequency of application should take into account the physical dimensions of the area to be treated, the rate of absorption and metabolism of all ingredients that are absorbed into the systemic circulation. The stage of the disorder to be treated, and what other pharmacological agents are administered concurrently.

"Non-toxic": As used herein, "non-toxic" refers to the administration of a dose of the composition for treatment of anal pain, wherein the active components in the composition cause no adverse effects intolerable to the patient onto which the composition is administered.

"Anorectal disease": The terms "anorectal disease", "painful conditions of the anal region", "anal conditions", "anal pain", and the like, are used herein to describe symptoms of discomfort or pain in a person's anorectal area, or the diseases and disorders that produce them. Anorectal diseases include anal fissures, thrombosed or inflamed hemorrhoids, pain associated with the after effects of anal surgery (such as rubber-band ligation of internal hemorrhoids) and chronic anal pain. The anorectal area comprises the anal mucosa, the mucosa of the most distal portion of the rectum, the internal and external anal sphincters, the skin immediately surrounding the anus.

"α-adrenergic blockers": "α-adrenergic blockers" is used herein synonymously with "α-adrenergic antagonists", and "α-antagonists". These terms are meant to encompass the α1-adrenergic antagonists, including doxazosin, prazosin and terazosin, as well as "non-specific α-adrenergic antagonists", including phentolamine and phenoxybenzamine, that have strong α1-adrenergic antagonism. Non-specific α-adrenergic antagonists can be used in the compositions of the present invention only if they have strong α1-adrenergic antagonism. Specific α2-adrenergic agents are not included. In this application, claims made for α1-adrenergic antagonists should be regarded as being made also for less specific α-adrenergic antagonists with strong α1-adrenergic antagonism.

"Active agent": "Active agent", as used herein, refers to any component in a composition of the present invention that increases the analgesic effects of that composition and can be added to the compositions of the present invention to enhance their ability to reduce the symptoms associated with anorectal disease. In the composition of the present invention, α-blockers, lidocaine and sucralfate are all active agents. "Active agent" is also used to refer to any component in any known composition (e.g. preparation H) that increase the analgesic effects of that composition.

"Active ingredient": "Active ingredient", differs from the use of "active agent", as used herein, to mean any component that can be added to a composition that has some biological effect, whether the biological effect is directly related to anorectal disease or not. The biological effect is preferably curative. Such components might have analgesic or anesthetic effects, for example, capsaicin, corticosteroids (hydrocortisone and triamcinolone), non-steroidal antiinflammatory drugs (including specifically diclofenac opiates), or salicylates (salsalate, sulfasalazine). Such components might alternatively have an activity unrelated to pain reduction. For example, such active ingredients as antibiotics, antifungals, or antivirals.

"Active compound": "Active compound" as used herein, encompasses both the drugs referred to as "active agents" and the drugs referred to as "active ingredients" defined herein. "Active compound" is used generally to refer to anything with relevant biological activity that is added to biologically inert ingredients in a composition intended for therapeutic use.

DESCRIPTION OF THE PREFERRED EMBODIMENT

As mentioned above, spasm of the IAS is a major source of pain in conditions of the anal region. Sympathetic nerves from the lumbar plexus have a major role in determining baseline IAS pressure as well as reflex increases in IAS pressure occurring in response to stimulation of nociceptive afferents from the anal region. Sympathetic nervous activity has been shown to be relevant to pain perception, and both clinical and experimental pain can be altered by drugs that affect the sympathetic nervous system. Specifically, clonidine, an α2-adrenergic agonist, has been shown in many studies to potentiate the analgesic effect of opiates, and to be an analgesic in its own right. Other α2-agonists, α1-antagonists, and non-specific α-adrenergic antagonists all have been shown to have analgesic effects. Conversely, yohimbine, an α2-antagonist, has been shown to aggravate pain in some animal models.

The effect of α-adrenergic drugs upon pain, however, is not consistent across all clinical and experimental situations. In a standard animal chronic pain model—the formalin test—systemic injections of α1-adrenergic agonists had an antinociceptive (analgesic) effect (Tasker et al., *Pain* 1992 June 49:383–91). The α1-adrenergic agonists ST 587 and methoxamine were shown to be antinociceptive in a rat model (Hayes et al., *Neuropharmacology,* 1986 April 25:391–6). In a mouse model of pain and analgesia, phentolamine, a nonspecific α-adrenergic blocker, diminished the analgesic effect of morphine (Slivko and Stets, Farmakol Toksikol, 1978 September–October, 41:544–8). In humans, neither α1-adrenergic agonists nor α1-adrenergic antagonists were superior to placebo in treating a group of patients with reflex sympathetic dystrophy. (Verdugo., Neurology, 1994 June 44:1003–10). The α1-adrenergic antagonists have analgesic effects in some (but certainly not all) kinds of experimental and clinical pain. For example, prazosin blocked local mechanical hyperalgesia produced in a rat model by injection of prostaglandin E2 and rolipram, a Type IV phosphodiesterase inhibitor. (Ouseph et al., Eur J Pharmacol., 1995 January 24 273:107–12).

The innervation of the internal anal sphincter (IAS) is complex, involving adrenergic, cholinergic, and non-adrenergic non-cholinergic nerves. In general, α-adrenergic stimulation contracts the sphincter, and β-adrenergic stimulation relaxes it. (Penninckx et al.; Baillieres Clin Gastroenterol, 1992 March 6:193–214; O'Kelly T, et al., Gut, 1993 34:689–93; May and Nissan et al., J Pediatr Surg, 1984 February 19:12–4; T+e,sez o+ee ttrup et al., Br J Pharmacol, 1995 May, 115:158–62,; Sumitomo et al., Z Kinderchir, 1986 February 41:35–8).

Contraction of the IAS in response to hypogastric (sympathetic) nerve stimulation, or spasm of the IAS in response to local stimulation, is attenuated by α1-adrenergic antagonists and by non-specific α-adrenergic antagonists. In its response to α-agonists and antagonists, the IAS responds like the internal urethral sphincter, with which it shares a common developmental origin. As expected, phenylephrine, an α1 agonist, increases tone in the IAS. However, it is unexpected that a tolerable dose of an α-adrenergic blocker by the anal route can provide enough relaxation for its application to be clinically useful. Indeed, the response of the internal anal sphincter to adrenergic stimulation is complex in both normal and pathological situations; it is influenced by, and has influences upon, several other neurotransmitters. (Hellstrm et al., Scand J Gastroenterol, 1989 March 24:231–43; Rayner, J Physiol (Lond), 1979 January 286:383–99; Bouvier and Gonella; J Physiol (Lond), 1981 January 310:457–69; Rattan and Thatikunta, Gastroenterology, 1993 September 105:827–36; Carlstedt et al.; Acta Physiol Scand, 1989 January 135:57–64,; Yoshimura et al.; Dig Dis Sci, 1986 November 31:1249–53) Moreover, basal anal canal pressure, at least in some species, does not depend on tonic adrenergic activity and is not altered by administration of an α-adrenergic blocker (Culver and Rattan, Am J Physiol, 1986 December 251:G765–71). And, in human subjects studied while under anesthesia for abdominal surgery, stimulation of the hypogastric sympathetic (adrenergic) nerves relaxed the IAS, and administration of an adrenergic blocking drug prevented the relaxation of the sphincter. (Lubowski, et al.; Br J Surg, 1987 August 74:668–70). Hence, it is by no means obvious that alpha blockade will reduce IAS pressure sufficiently to receive pain and promote healing.

I conceived of the idea of using a topical preparation of an α1-adrenergic antagonist or a nonspecific α-adrenergic antagonist to reduce IAS pressure and thereby relieve pain in individuals with anal fissures and other acute, painful conditions of the anal region. I prepared a topical cream containing doxazosin, an α1-adrenergic blocker, in a lubricant base that made of petrolatum and K-Y jelly. The concentration of doxazosin in this preparation was 0.2 mg/ml of cream.

The cream was administered to a patient with an anal fissure and severe acute pain (see Case Report 3). Within 5 minutes, she had substantial relief—>50%. She compared the cream with a combination cream containing nitroglycerin, lidocaine and sucralfate; results were similar. The patient had a headache after applying the cream with nitroglycerin, but did not experience any adverse side effects from the cream containing doxazosin. She therefore chose to continue using the doxazosin cream. This demonstrated the analgesic effect of an α1-adrenergic antagonist for the pain of anal fissure. One can infer that a nonspecific α-adrenergic antagonist would also be effective, since its α-2 antagonist effects would not be expected to interfere with the relaxation of anal sphincter spasm from its α-1 antagonist effects. (This case also demonstrates that in some individuals, an effective dose of an α1-adrenergic antagonist can have less toxicity than an effective dose of nitroglycerin.)

As noted above, in co-pending patent application Ser. No. 09/031,858, I reported that a cream containing nitroglycerin, lidocaine, and sucralfate was efficacious for the treatment of the pain of anal fissures, and that it was more efficacious than nitroglycerin alone, or nitroglycerin with lidocaine, lidocaine and sucralfate alone, or nitroglycerin and sucralfate alone.

Three factors contribute to the synergistic efficacy of the combination: 1) the local anesthetic effect of lidocaine is based on a different mechanism of action than the analgesic effect of nitroglycerin; 2) sucralfate serves to keep the other two ingredients adherent to the fissure, prolonging their action; 3) sucralfate has antiinflammatory effects in its own right. Given the efficacy of an α1-adrenergic blocker alone for anal pain, I inferred that the combination of an α1-adrenergic blocker with lidocaine and sucralfate, or with lidocaine or sucralfate alone, would provide relief from anal pain. Such combination would circumvent the use of nitroglycerin, which, as noted above, causes adverse side effects, especially headaches, in some patients. In addition, the combined use of an α-adrenergic blocker with lidocaine and sucralfate provides therapeutic efficacy at a lower than toxic dose of the α-adrenergic blocker due to the synergistic activity of the three compounds in treating anal pain. (In general, α-adrenergic blockers are particularly promising in combination preparations, because their already low toxicity is even less at the lower doses required in combinations with synergistic or even additive efficacy.)

The present application demonstrates the use of a topical preparation of an α1-adrenergic blocker (e.g., doxazosin, prazosin or terazosin) to reduce IAS pressure with greater effect on reflex spasm than on baseline pressure (see Case reports 3, 4 and 5). It is evident that the α1-adrenergic blocker could be replaced by a less specific α-adrenergic blocker, (e.g., phentolamine or phenoxybenzamine), preferably one with prominent α1 adrenergic blocking effects.

In one preferred embodiment, the α1-adrenergic blocker is used alone. Alternatively the α1-adrenergic blocker is combined with a local anesthetic for treatment of painful anal conditions. One skilled in the art will recognize any local anesthetic, such as, without limitation, lidocaine, benzocaine, dibucaine bupivacaine, tetracaine etc., is acceptable for use in the present invention. Preferred local anesthetics include lidocaine, benzocaine, dibucaine, and bupivacaine. A most preferred local anesthetic is lidocaine.

In other preferred embodiments, the α-adrenergic blocker is combined with sucralfate for the treatment of painful anal conditions. It will be obvious to one of ordinary skill in the art that sucralfate can, of course, be replaced by any disaccharide-polysulfate aluminum compound with similar physical and pharmacodynamic properties. In yet another preferred embodiment of the present invention, the α-adrenergic blocker is combined with both a local anesthetic and sucralfate or similar anti-inflammatory, as mentioned above, for application to the anal region.

It is preferable that any composition described herein is administered at effective and non-toxic dosages, such that the patient experiences relief from symptoms in the absence of any undesirable side effects. In the compositions of the present invention, the an α1-antagonist of the same potency of terazosin or doxazosin would be administered in the dose range of 0.1–1.0 mg per 5 ml of formula. A local anesthetic of the same potency as lidocaine would be administered at a concentration in the dose range of 20–200 mg per 5 ml of formula. Sucralfate is typically administered at 50–500 mg per 5 ml of formula. A particularly preferred composition of the present invention is a composition in which each standard 5 ml dose contains 0.1–1.0 mg of doxazosin or terazosin, 20–200 mg of lidocaine, and 50–500 mg of sucralfate. Specific concentrations may be adjusted according to patient tolerance. Dosage in individual patients—regarding the concentration of the ingredients, the amount to be applied with each application, and the frequency of application, should take into account the physical dimensions of the area to be treated, and rate of absorption and metabolism of all ingredients that are absorbed into the systemic circulations, the stage of the disorder to be treated, and what other pharmacological agents are administered concurrently.

Another aspect of the present invention provides compositions containing α-adrenergic blockers and additional active ingredients. One particularly attractive active ingredient of the present inventive composition is capsaicin.

Pain transmission from inflamed areas is transmitted in part by neurons that have Substance P as a neurotransmitter. Capsaicin, a compound that depletes neurons of Substance P, has been used to relieve pain due to inflammation. Capsaicin initially was used as a topical preparation for the skin that was either inflamed itself, or for skin overlaying inflamed joints or soft tissues. Subsequently a capsaicin candy was developed for the treatment of mouth pain due to inflammation. U.S. Pat. No. 5,788,982 by Nadoolman, et al., and U.S. Pat. No. 4,997,853 by Bernstein describes co-administration of capsaicin and lidocaine generally to the skin, to reduce the burning associated with the application of capsaicin alone. U.S. Pat. No. 5,854,291 by Laughlin et al., describes use of capsaicin in conjunction with a topical anesthetic for treatment of hemorrhoidal pain and itching. Capsaicin is a desirable active ingredient for treatment of anal pain, not only because it has analgesic effects, but because continued capsaicin treatment, by partially and reversibly denervating the anal region, reduces some of the reflex contractions of the rectum that can create an uncomfortable sense of fecal urgency in an individual with a painful anal condition. Thus, I proposed that the active ingredient capsaicin may be added to any composition for treatment of anal pain.

In preferred embodiments, capsaicin is administered at such dose that is tolerable and minimizes the burning sensation associated with application to mucus membranes. Particularly, capsaicin is combined with any agent that reduces the initial burning sensation associated with the application of capsaicin to mucous membranes (see Case Report 6), especially mucous membranes of the anal region. More preferably, capsaicin is combined with a local anesthetic at such dose that the capsaicin is effective at reducing pain in the anal region, yet is tolerable upon application. Any persisting initial discomfort associated with capsaicin application is eventually replaced by long-term relief of inflammatory pain, via depletion of Substance P from the local. In a particularly preferred embodiment, capsaicin (at a tolerable dose or with a local anesthetic) is combined with an α1-adrenergic antagonist for treatment of anal pain.

The present invention also provides other active ingredients that may be combined with the α1-adrenergic blocker for treatment of anal pain. For example, the α-adrenergic blocker can be combined with antibiotics, antifungals, antivirals, corticosteroids (e.g., hydrocortisone or triamcinolone), non-steroidal antiinflammatory drugs (including specifically diclofenac or COX-2 inhibitors such as nimesulide or piroxicam), or salicylates (e.g., salsalate or sulfasalazine). The analgesic effects of the combination of α-adrenergic blocker with an additional active ingredient can be enhanced further by the addition of either a local anesthetic, sucralfate or both. Such compositions may be applied to the anal region at effective and non-toxic dosages for treatment of anal pain.

In other preferred embodiments, a topical formula for treatment of anal fissures and other painful anal conditions involving spasm of the IAS containing α-adrenergic antagonists is supplemented with ingredients that together with the α-adrenergic antagonist have synergistic effects in treating anal pain. For example, an α-adrenergic antagonist can be combined with at least one, preferably any two of a steroidal antiinflammatory (e.g., a corticosteroid), a non-steroidal antiinflammatory drug (including specifically diclofenac opiates), a local anesthetic, sucralfate or a similar disaccharide, capsaicin (with a local anesthetic, i.e., lidocaine) or capsaicin (in a tolerable dosage or preparation). Such combinations would provide improved relief over treatment with the α-antagonist alone.

Because spasm of the IAS is a common mechanism of pain in all acute painful conditions of the anal regions, α1-adrenergic antagonists, alone or in any of the above-mentioned combinations, will be efficacious and tolerable in therapies for other painful anal conditions, including without limitation anal ulcer, inflamed or thrombosed hemorrhoids, and status-post rubber band ligation of hemorrhoids.

The compositions of the present invention are applied topically to the anorectal area to obtain relief from the above mentioned symptoms. The compositions are applied topically to the involved area until the symptoms are relieved. The compositions are administered once or several times over the course of a single day. The administration is continued for as many days as are necessary to relieve the condition being treated. It will be obvious to one of ordinary skill in the art that the compositions of the present invention can be applied anywhere on the body for treatment of pain.

In a particularly preferred embodiment of the present invention, an α-adrenergic blockers is used to replace or augment the active agents in various known marketed over-the-counter compositions for treatment of anorectal conditions, including without limitation Anusol, Tronolane, Preparation H, and generic equivalents of those products. Other examples are A-Caine, Americane, Anusol, Balneol, BiCozene, Blue-Gray, Calmol 4, Cortef Rectal Itch Ointment, Diothane, Epinephiricaine Ointment, Gentzy Wipes, Hemorrin, HTO Ointment, HTO Stainless, Lancane, Mediconet, Non-Steroid Protofoam, Nupercainal Ointment, Nupercainal Suppositories, Pazo, Perifoam, Peterson's Ointment, Pontocaine, Preparation H Cleansing Pads, Proctodon, Rantex, Rectal Medicone Suppositories, Rectal Medicone Unquent, Tanicaine Ointment, Tanicaine Suppositories, Tucks Cream and Ointment, Tucks Pads, Wyanoid Ointment and Wyanoid Suppositories. See also Federal Register, 45 33576, May 22, 1980.

The α-adrenergic blocker could also be added to marketed over-the-counter compositions that do not have an active compound, including petrolatum (Vaseline), K-Y Jelly, lanolin, mineral oil, cocoa butter, calamine, glycerin, kaolin, and cod liver oil. α-adrenergic blockers could replace any active agent with a principal action of relieving IAS spasm or reducing IAS pressure, including without limitation nitroglycerin, other nitrates (e.g. isosorbide dinitrate), other nitric oxide donors, and L-arginine. Any composition containing any one of these ingredients could be reformulated to contain an α-adrenergic blocker, (i.e., an α1-adrenergic antagonist or a non-specific α-adrenergic antagonists with sufficient α1-adrenergic antagonist effects.). Alternatively, capsaicin, with or without a local anesthetic such as lidocaine, can be used to replace the active agents or ingredients in the above-mentioned marketed over-the-counter compositions.

Alternatively, the α-adrenergic antagonist is administered to a patient with the symptoms of anorectal disease in conjunction with the administration of a known product therapeutically helpful in the symptomatic treatment of anorectal disease. Examples of over-the-counter products which can be administered with α-adrenergic antagonists include but are not limited to, Anusol, Tronolane, Preparation H, and generic equivalents of those products.

The main pharmacologic compounds formulated in the above products include local anesthetics, vasoconstrictors, protectant, counterirritants, astringents, wound healing compounds, antiseptics, keratolytic and anticholinergics. See also Federal Register 45 35576, May 27, 1980. It is within the scope of the instant invention that an α-adrenergic antagonist is administered in combination with any or all of these compounds. Preferred compounds include those known as topical anesthetics, protectants, vasoconstrictors and would healing compounds.

As mentioned above, local or topical anesthetics temporarily relieve pain, burning, itching, discomfort and irritation by preventing transmission of nerve impulses. Non-limiting examples of topical anesthetics include benzocaine, pramoxine hydrochloride, benzyl alcohol, dibucaine hydrochloride, dicylonine hydrochloride, lidocaine, tetracaine and tetracaine hydrochloride. See also Federal Register, 45 35576, May 27, 1980. In general, the local or topical anesthetic may be present in any amount which is effective in the practice of the treatment of anal disease.

Protectants act to prevent irritation of the anorectal area and water loss from the skin layer by forming a physical barrier on the skin. There is little or no absorption of the protectants. Non-limiting examples include aluminum hydroxide gel, calamine, cocoa butter, cod liver oil, glycerin, kaolin, lanolin, mineral oil, shark liver oil, starch, white petrolatum, wood alcohol and zinc oxide. See also Federal Register, 45 35576, May 27, 1980.

Vasoconstrictors act to reduce inflammation, irritation and swelling by constricting the symptomatic abnormally large conglomerates of blood vessels. Non-limiting examples include ephedrine and epinephrine. See also Federal Register, 45 35576, May 27, 1980.

In non-prescription hemorrhoidal products, several ingredients are claimed to be effective in promoting wound healing or tissue repair in anorectal disease. Non-limiting examples of would healing compounds include skin respiratory factor (SRF), a water soluble extract of brewer's yeast also referred to as live yeast cell derivation, cod liver oil, vitamin A and vitamin D. See Also Federal Register, 45 35576, May 27, 1980.

In certain preferred embodiments of the invention, α1-adrenergic agonists, capsaicin and other pharmacologic compounds used in the treatment of the symptoms of anorectal disease are formulated in the same composition, for example with a wound healing compound, a protectant, a vasoconstrictor, or a local anesthetic or with more than one of these compounds.

Compositions in the form of ointments, creams, gels, pastes, suppositories, pads, liquids, emulsions, foams, aerosols, semisolid powders, or any other composition suitable for topical administration are acceptable compositions for the topical treatment of the anorectal pain. In another aspect, the composition of the invention may contain conventional materials and ingredients and conform to pharmacologically accepted formulations. Some of the compositions listed above (e.g. creams, lotions, ointments and gels) may be used in the inventive compositions as thickening agents to create highly convenient dosage forms. Thickened solutions permit release of the active compound to the skin or tissue upon or following application. These forms are advantageously employed to lessen the runoff from the skin or tissue, that can occur with more fluid (less viscous) formulations. Importantly, they also permit more sustained contact of the active compound(s) and any penetration enhancer with the treated surfaces, thus permitting an enhancement of the speed of delivery of the active compound(s) to the inflamed tissues and sphincter muscle fibers, and providing more accurate and controllable dosing. Accidental spilling and undesired contact with the composition can also be minimized with such types of formulations.

It can be advantageous to employ water-dispersible thickening agents, i.e., agents dispersible in water to form a homogeneous distribution or even solution, such as the polyethylene glycols and similar agents, as they are readily compatible with water or other diluents which may be formulated in the composition. Alternatively, an emulsion base may be employed to impart the desired thickening effect, as well as the emollient effect of the lipoid phase of the emulsion base.

Water-soluble or water-dispersible thickening bases or substances may employ polyethylene glycols and the like of different viscosities depending upon the desired consistency and concentration of active compound(s) which may be incorporated into the composition. Other thickening agents which may be suitable for employment herein include but are not limited to water-dispersible gums, carboxyvinyl polymers, methyl cellulose, sodium carboxymethyl cellulose, and alginates.

Pourable pharmaceutical dosages may be provided and dispensed in graduated containers, or in containers which contain a given volume, say, for example, 5 or 10 cc. and so forth. Containers with greater volumes, say, for example, of 20 cc and greater, can provide convenient multiple dosage forms. Containers containing a typical single dose, for example, from about 0.5 g to about 10 g of active compound (s), can provide convenient dosage forms. Squeeze tubes for lotions and ointments and cofton stick applicators may be employed for topical application of the composition for liquids ranging from those of water-like viscosity of the more viscous formulations of thickened compositions and for powders and the like.

In treatments according to the invention, an amount of the composition of the invention is contacted with or applied to the affected anal area or proximate thereto such that an effective amount of α-adrenergic antagonist or other active compound is administered. The amount of active compound (s) or composition which is employed should be effective for the amelioration, control and/or healing of the anal disease and for the prompt and dramatic control or relief of pain resulting from or associated with the disease. For example, an ointment composition of the invention can be applied topically at each application to the external anus and to the distal anal canal with the finger or an applicator. As an illustrative alternative, the medication can be delivered rectally as a suppository. The medication can be applied in this fashion, for example, three or more times daily in the case of the ointment or once or more times daily in the case of the suppository.

In preparing the desired pharmaceutical form of the present compositions, various additives, diluents and adjuvants can be utilized. These illustratively include perfumes, essential oils, surfactants, ointment type bases, higher fatty acids, propellants, thickening agents, humectants, and silicone-type fluids as are known in the art.

The present invention will now be illustrated by the following non-limiting examples.

Treatment with Nitroglycerin Containing Compositions

Case Report 1: A 49-year old man had a chronic anal fissure, which had persisted for several months, producing chronic rectal pain relieved only by narcotic analgesics. Anoscopy, performed separately by a rectal surgeon and a gastroenterologist, confirmed the presence of a moderately large anal fissure. The surgeon thought that surgery was necessary, and the gastroenterologist proposed cauterization. Neither felt that the fissure would heal without invasive treatment of some kind.

The patient was first treated with nitroglycerin cream, 0.5%. (The cream was prepared by diluting 2% nitroglycerin ointment with a K-Y™ Jelly. This gave substantial but not complete pain relief that lasted about 2 hours, after which the pain gradually returned. Over several weeks, pain was relieved every time the cream was applied, but returned if it was stopped. He was then switched to the combination of nitroglycerin and sucralfate. With this combination, relief lasted 3–4 hours at first, and then lasted longer and longer with repeated applications. Within two weeks, he had full relief applying the cream only twice a day. Within six weeks, the symptoms were totally relieved and the analgesic cream was no longer necessary.

Case Series 2: 4 subsequent patients, all but one with anoscopically confirmed anal fissures, were treated with the combination of nitroglycerin, lidocaine, and sucralfate, with the expectation of even better relief. (Patient #4 suffered from chronic anal pain of unknown cause.) All 4 of those treated obtained relief, and all chose to continue the medication for several days. Patients were instructed to use the cream as often as they needed for pain relief they found satisfactory. The following table summarizes these patients' reports of their experience with the analgesic cream:

| Patient: Sex and age | 1: ♀ 47 | 2: ♀ 37 | 3: ♂ 69 | 4: ♂ 54 |
|---|---|---|---|---|
| Duration of pain before | 1 week | 2 weeks | 5 weeks | 2 years of |
| Other treatment tried | None | Generic | Anusol ™, | None |

| Patient: Sex and age | 1: ♀ 47 | 2: ♀ 37 | 3: ♂ 69 | 4: ♂ 54 |
|---|---|---|---|---|
| Time from application to | 30 minutes | 5 minutes | 30 minutes | 5–10 |
| Percentage of pain | 25% | 50% | 50% | No pain |
| Times a day applied | 2 | 2–3 | 2 | 2 |
| Persistence of benefit | Yes | Yes | Yes | Yes |
| Resolution of painful | Yes | Yes | Yes | Partial |
| Time to resolution of | 2 weeks | 1 week | 1 week | Severe pain |
| Side effects | Headache | Headache, | None | Burning |
| Stopped medication | No | No | No | No |
| Persistence of side effects | No | Yes | N/A | No |

Five patients, all with anoscopically confirmed fissures, received jars of the analgesic cream, and were instructed to apply it as needed to eliminate their pain. All got complete relief within minutes. The complete relief they obtained contrasted with the partial relief usually reported by patients treated with nitroglycerin ointment alone. Applications about four times daily were adequate to completely control their pain. Three of the patients had been scheduled for surgery to treat their fissures. They had been given the cream 3 to 4 weeks before the date planned for the operation. All three patients canceled their operations, because they had sufficient pain relief. One underwent repeat anoscopy, which revealed complete healing of the fissure.

None of the 5 patients required any oral analgesics, sitz baths, or other treatments to relieve pain, as soon as they had access to the nitroglycerin-lidocaine-sucralfate cream.

An additional experiment was performed to establish the effect of the sucralfate. A 64 year old man with severe pain following the rubber band ligation of a hemorrhoid was treated. He had six weeks of pain prior to the treatment. We treated him on alternate days with either the composition including nitroglycerin, lidocaine and sucralfate or the composition without the sucralfate. He was instructed to reapply the formula any time the pain began to recur. The three ingredient formula gave 90% relief (i.e., pain reduced to 10% of baseline) within fifteen minutes. The patient applied the cream three more times during the next twenty-four hours obtaining satisfactory relief.

The formulation without sucralfate gave less relief, and the pain recurred sooner. The patient applied the two-ingredient (without sucralfate) formula a total of five more times during the next twenty-four hours. Not only did the three-ingredient (with sucralfate) formula act faster, but it was associated with a less severe headache than the two-ingredient formula. The two-ingredient formula may have caused a worse headache because the patient might have used more of it to get relief. Alternatively, the sucralfate in the three-ingredient formula may have slowed the systemic absorption of nitroglycerin.

An additional three patients (Patients 5, 6, and 7) were treated with various formulations to establish the benefit of sucralfate and to illustrate that the concentration of nitroglycerin needed to treat anal fissure can be lower than that reported in the literature. These cases also show that adding nitroglycerin to the sucralfate-lidocaine combination improves efficacy. The three additional cases are shown in the table below:

| Patient: Sex and age | 5: ♀ 68 | 6: ♂ 81 | 7: ♂ 33 |
|---|---|---|---|
| Diagnosis | Anal | Anal fissure | Inflamed |
| Duration of pain before | 6 months | 3 months | 2 months |
| Other treatment tried | None | Sitz baths, | Desitin |
| Time from application to | 30 minutes | 15 minutes | 5 minutes |
| Percentage of pain | 25% | 70% after | Complete |
| Times a day applied | 5 | 2–3 | 3–4 |
| Persistence of benefit | Yes | Yes | Yes |
| Resolution of painful | Yes | Yes | Yes, but it |
| Time to resolution of | Not known | 4 weeks | Not known |
| Side effects | None | None | No |
| Stopped medication | No | No | No |
| Persistence of side effects | N/A | N/A | N/A |

Patient #5 in the table above received the nitroglycerin-lidocaine-sucralfate formula discussed above (formula A) and a formulation without sucralfate (formula B) in the sequence A-B-A over three days. The reported benefit shown in the table above resulted from use of formula A. Formula B was not tolerated; it produced a throbbing headache. This case suggests that sucralfate may actually provide some protection against nitroglycerin-induced headache, perhaps by influencing the absorption of the nitroglycerin.

Patient #6 received a modified formula with 30 grams of 2% nitroglycerin ointment per 500 grams of the nitroglycerin-lidocaine-sucralfate mixture. The concentration of nitroglycerin in this mixture (0.12%) was lower than the 0.2% concentration reported in recent randomized controlled trials of the use of nitroglycerin as a single compound. Nonetheless, the mixture was efficacious and did not cause headaches (or any other side effects). This case supports the inventor's premise that nitroglycerin in combination with sucralfate and lidocaine is superior to nitroglycerin alone. The combination is efficacious at lower doses of nitroglycerin and the combination is less likely to cause headache.

Patient #7 received formula A and a formulation without nitroglycerin (formula C) in the sequence A-C-A over three days. This formula C (without nitroglycerin) did not give complete relief; the patient estimated that 25% of the pain remained after application. This case supports the relevance of nitroglycerin to the analgesic activity of the mixture, even in conditions other than anal fissure, where the efficacy of nitroglycerin is well established.

Conclusions: A topical analgesic cream or ointment for anal fissures that contains nitroglycerin will be more efficacious if it also contains sucralfate. A cream or ointment containing nitroglycerin, sucralfate, and lidocaine is especially efficacious.

Treatment with α-adrenergic Blockers

Case Report 3: A topical cream containing doxazosin, an α-adrenergic blocker, at a concentration of 0.2 mg/ml in a lubricant base made of petrolatum and K-Y™ Jelly was administered to a female patient with an anal fissure and severe acute pain of the anal region. Within 5 minutes, the patient has substantial relief (>50%). The patient compared the α-adrenergic cream with a cream containing nitroglycerin, lidocaine and sucralfate and reported that relief was similar. The patient chose to continue using the doxazosin cream.

I next prepared a formula consisting of:
240 grams petrolatum
180 grams K-Y Jelly
10 grams lidocaine base
30 grams sucralfate
100 mg doxazosin Each dose of approximately 5 grams contained 1 mg of doxazosin.

This formula was tested in 2 patients (Case Reports 4 and 5) with pain from anal fissures.

Case Report 4: A 39 year-old woman had had rectal pain for several months due to an anal fissure. Treatment with hydrocortisone did not give adequate relief. After application of the cream she had complete relief of pain within 1–3 minutes. The cream was applied twice a week. After 2 weeks her pain was almost gone, with only occasional pain before she was due for an application of the cream. Thereafter, she continued on the cream. Her final report on her use of the cream was after 6 weeks. At that point it continued to work as well as at the beginning, and the pain that was occasionally present was only 40% as severe as it was before starting the cream. No side effects were reported. In particular, she had no headaches, faintness, dizziness, or burning sensations at the site of application.

Case Report 5: A 53 year-old woman had had 2 months of pain from a rectal fissure, with inadequate relief from Tronolane® cream, warm baths, and hydrocortisone suppositories. She applied the cream and got complete relief of the pain "almost immediately." The cream was continued twice a day for the 4 weeks. She was virtually pain-free throughout the 4 weeks, using the cream twice a day. She reported having "almost no" pain when she would get up in the morning, before applying the cream. When she first used the cream, she got a headache and a light-headed feeling. These symptoms were no longer present by the third day of use. There were no other side effects.

Conclusions: Case Reports 4 and 5 establish that a combination of lidocaine, sucralfate and an α1-adrenergic antagonist is efficacious and tolerable treatment for anal fissures. Together with Case Report 3, showing that an α1-adrenergic antagonist alone is efficacious, it can be inferred that the combination of an α1-adrenergic antagonist with either sucralfate or lidocaine (rather than both) will be efficacious.

Tolerability of Capsaicin in a Formula Containing a Local Anesthetic

Case Report 6: To evaluate the potential usefulness of capsaicin in the anal region, I did an experiment on the tolerability of capsaicin alone and with lidocaine, and with lidocaine and dozasosin. A small amount of 0.075% capsaicin cream amount (about 5 mm of Zostrix® cream, as it comes from the tube) was applied to the anal area, reaching 1 cm past the external anal sphincter. The cream produced an intolerable burning sensation, relieved only by removing the cream and washing the area with copious amounts of water. The same amount of capsaicin cream was then combined with an equal amount of 5% lidocaine-prilocaine cream (EMLA® Cream), The burning sensation was present, but was tolerable. Finally, the same amount of capsaicin cream was combined with the above described doxazosin-lidocaine-sucralfate cream. The burning sensation was less than with the EMLA Cream, and was easily tolerated.

Conclusion: Administration of 0.075% capsaicin cream alone to the anal region is intolerable, but if it is combined with a local anesthetic ingredient that reduces the initial burning sensation, it becomes tolerable. Once it is made tolerable by the concurrent presence of a local anesthetic, capsaicin, with its known local analgesic properties, becomes a safe and effective active ingredient in a composition for the relief of anal pain. It would be expected to augment the effects of ingredients that work by different mechanisms of action (i.e., mechanisms not based on depletion of Substance P.).

Discussion: The Case Reports and Case Series above demonstrate three important points regarding compositions for the relief of painful conditions of the anorectal region. 1) Combinations of three (or more) ingredients that have different mechanisms of action may be therapeutically superior to single agents, or combinations of two agents. In particular, the combination of nitroglycerin or an α1-adrenergic blocker with sucralfate and lidocaine is particularly effective. Preparations of superior effectiveness combine an agent that relieves spasm of the IAS with a local anesthetic and with an agent with antiinflammatory and/or protective properties. 2) Nontoxic doses of alpha 1-adrenergic blockers, such as doxazosin, can relax spasm of the IAS to a sufficient degree to relieve pain. They thus can replace other IAS relaxants, e.g. nitrates, in compositions for the relief of anorectal pain. Or, they can be use to augment the relief provided by compositions that do not include an IAS relaxant. 3) Capsaicin, which by itself is intolerable by the rectal route of administration, becomes tolerable when given in combination with a local anesthetic. It thus can be a useful addition to a composition for the treatment of anorectal pain, as long as that composition contains a local anesthetic ingredient.

Other anal and rectal conditions, such as inflamed hemorrhoids, produce pain for the same reasons as an anal fissure, a combination of inflammation and spasm of the anal sphincter. Therefore, a combination cream or ointment that is effective for the pain of anal fissures is expected to be similarly helpful for the pain of inflamed hemorrhoids. This is demonstrated by patient #3 in Case Series 2, above and as demonstrated in patient #7 in Case Report 2 above. The cream or ointment may also provide relief for pain following rubber band ligation of internal hemorrhoids, as this procedure often leads to sphincter spasm and local inflammation.

A triple combination of nitroglycerin, sucralfate, and lidocaine (or more generally a nitrate, sucralfate, and a local anesthetic) will produce more rapid, complete, and long-lasting relief than a composition with only one or two of the three ingredients. A triple combination of an alpha 1-adrenergic blocker, sucralfate, and a local anesthetic will produce more rapid, complete and long-lasting relief than a composition with only one or two of the three ingredients. Despite the availability of all of these ingredients for many years, and recent patents regarding the use of nitroglycerin and the use of sucralfate in the anal region, the use of the combination has not been reported. No one has hitherto suggested that a triple combination containing nitroglycerin will have lesser side effects than an equally effective dose of nitroglycerin alone. Experience with the combination of nitroglycerin, lidocaine, and sucralfate suggests that it does have less side effects than nitroglycerin, either because less nitroglycerin is used by the patient to get relief, or because the nitroglycerin is absorbed more slowly.

The use of alpha 1-adrenergic blockers to relieve the pain of anorectal conditions is, to our knowledge, completely novel. Further, effective doses of alpha 1-adrenergic blockers appear less likely to cause headaches or hypotension than equally effective doses of nitroglycerin. Thus, alpha 1-adrenergic blockers may find extensive use in the enhancement of the efficacy of compositions for the treatment of anorectal pain.

What is claimed is:

1. A method for treating a patient with a painful condition of the anal region associated with muscle spasm, the method comprising steps of:
   providing a composition comprising an α-adrenergic blocker; and
   applying an effective dose of the composition to the anal region.

2. A method for treating a patient with a painful condition of the anal region associated with muscle spasm, the method comprising steps of:
   providing a composition comprising an α-adrenergic blocker and sucralfate; and
   applying an effective dose of the composition to the anal region.

3. A method for treating a patient with a painful condition of the anal region associated with muscle spasm, the method comprising steps of:
   providing a composition comprising an α-adrenergic blocker and a local anesthetic; and
   applying an effective dose of the composition to the anal region.

4. A method for treating a patient with a painful condition of the anal region associated with muscle spasm, the method comprising steps of:
   providing a composition comprising an α-adrenergic blocker, a local anesthetic and sucralfate; and
   applying an effective dose of the composition to the anal region.

5. A method for treating a patient with a painful condition of the anal region associated with muscle spasm, the method comprising steps of:
   providing a composition comprising an α-adrenergic blocker, a local anesthetic and capsaicin; and
   applying an effective dose of the composition to the anal region.

6. The method of claim 1, 2, 3, 4, or 5, wherein the step of providing, the α-adrenergic blocker is an $\alpha_1$-adrenergic antagonist.

7. The method of claim 6, wherein $\alpha_1$-adrenergic antagonist is selected from the group consisting of: doxazosin, prazosin, and terazosin.

8. The method of claim 1, 2, 3, 4, or 5, wherein the α-adrenergic blocker is a non-specific α-adrenergic antagonist.

9. The method of claim 8, wherein the non-specific α-adrenergic antagonist is selected from the group consisting of: phentolamine and phenoxybenzamine.

10. The method of claim 3, 4 or 5, wherein the local anesthetic is selected from the group consisting of: lidocaine, benzocaine, bupivacaine, and tetracaine.

11. The method of claim 1, 2, 3, 4, or 5, wherein after the step of providing and before the step of applying, the method further comprises the step of:
    mixing the composition with a cream, gel, paste, lotion, ointment, aerosol, suppository, pad, liquid, emulsion, foam or, semisolid powder or a combination thereof.

12. The method of claim 1, 2, 3, 4, or 5 wherein the composition further comprises a cream, gel, paste, lotion, ointment, aerosol, suppository, pad, liquid, emulsion, foam or semisolid powder or a combination thereof.

13. The method of claim 1, 2, 3, 4, or 5 wherein the painful condition is an anal fissure.

14. The method of claim 1, 2, 3, 4, or 5 wherein the painful condition is thrombosed hemorrhoid or inflamed hemorrhoid.

15. The method of claim 1, 2, 3, 4 or 5 wherein the painful condition results from rubber band ligation of internal hemorrhoids or recent surgery involving the anal region.

16. A method for treating a patient with a painful condition of the anal region associated with muscle spasm, the method comprising steps of:
   providing a composition comprising an α-adrenergic blocker, a local anesthetic and sucralfate in a base of petrolatum, and further comprising a water soluble lubricant; and
   applying an effective dose of the composition to the anal region.

17. The method of claim 16 wherein the composition comprises approximately 0.1–1.0 milligrams of doxazosin or terazosin per 5 milliliters of composition, approximately 20–200 milligrams of lidocaine base per 5 milliliters of composition, and approximately 50–500 milligrams of sucralfate per 5 milliliters of composition.

18. The method of claim 16 wherein the local anesthetic is lidocaine.

19. The method of claim 16, wherein the α-adrenergic blocker is an $\alpha_1$-adrenergic blocker.

20. The method of claim 16, wherein the α-adrenergic blocker is selected from the group consisting of: doxazosin, prazosin, and terazosin.

21. The method of claim 19, wherein the $\alpha_1$-adrenergic blocker is a non-specific α-adrenergic antagonist.

22. The method of claim 16, wherein the α-adrenergic blocker is a non-specific α-adrenergic antagonist selected from the group consisting of: phentolamine and phenoxybenzamine.

* * * * *